(12) United States Patent
Ray et al.

(10) Patent No.: US 10,247,652 B2
(45) Date of Patent: *Apr. 2, 2019

(54) CONTROLLED SAMPLING VOLUME OF CLOUDS FOR MEASURING CLOUD PARAMETERS

(71) Applicant: Rosemount Aerospace Inc., Burnsville, MN (US)

(72) Inventors: Mark Ray, Burnsville, MN (US); Kaare Josef Anderson, Farmington, MN (US)

(73) Assignee: Rosemount Aerospace Inc., Burnsville, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/961,761

(22) Filed: Apr. 24, 2018

(65) Prior Publication Data

US 2018/0313736 A1    Nov. 1, 2018

Related U.S. Application Data

(63) Continuation of application No. 15/411,548, filed on Jan. 20, 2017, now Pat. No. 9,983,112.

(51) Int. Cl.
*G01N 15/06* (2006.01)
*G01N 15/02* (2006.01)
(Continued)

(52) U.S. Cl.
CPC ......... *G01N 15/0205* (2013.01); *B64D 15/20* (2013.01); *G01N 15/06* (2013.01);
(Continued)

(58) Field of Classification Search
CPC .................................. B64D 15/20; G01W 1/00
See application file for complete search history.

(56) References Cited

U.S. PATENT DOCUMENTS 5,028,929 A * 7/1991 Sand ..................... G01S 13/106
342/26 B
5,239,352 A * 8/1993 Bissonnette .......... G01S 7/4816
356/5.01
(Continued)

OTHER PUBLICATIONS

Ray, Mark et al., "Optical Detection of Airborne Ice Crystals and Liquid Water Droplets", American Institute of Aeronautics and Astronautics, 2009, 15 pages.
(Continued)

*Primary Examiner* — Shawn Decenzo
*Assistant Examiner* — Jarreas C Underwood
(74) *Attorney, Agent, or Firm* — Kinney & Lange, P.A.

(57) ABSTRACT

Apparatus and associated methods relate to determining a size and/or density of Super-cooled Large Droplets (SLDs) in a cloud atmosphere by comparing detected optical signals reflected from small and large sampling volumes of a cloud atmosphere. In some embodiments, an optical pulse is generated and divergently projected from a first optical fiber. A collimating lens is aligned within the divergently projected optical pulse collimating a portion thereof. The collimated and uncollimated portions of the optical pulse are projected into the small and large sampling volumes of the cloud atmosphere, respectively. The ratio of the collimated to the uncollimated portions can be optically controlled. Signals corresponding to optical pulses having different collimated/uncollimated ratios are backscattered by the cloud atmosphere, detected and compared to one another. A processor is configured to calculate, based on scintillation spike differences between the optical pulses of different collimated/uncollimated ratios, a size and/or density of SLDs.

20 Claims, 9 Drawing Sheets

(51) Int. Cl.
*G01W 1/00* (2006.01)
*B64D 15/20* (2006.01)
*G01S 17/95* (2006.01)
*G01S 7/481* (2006.01)
*G01N 15/00* (2006.01)

(52) U.S. Cl.
CPC ........... *G01S 7/4811* (2013.01); *G01S 7/4815* (2013.01); *G01S 7/4818* (2013.01); *G01S 17/95* (2013.01); *G01W 1/00* (2013.01); *G01N 2015/0026* (2013.01); *G01N 2015/0277* (2013.01); *G01N 2015/0693* (2013.01)

(56) References Cited

U.S. PATENT DOCUMENTS

| | | | |
|---|---|---|---|
| 6,839,485 B2 | 1/2005 | Gardner et al. | |
| 7,741,618 B2 | 6/2010 | Lee et al. | |
| 8,144,325 B2 | 3/2012 | Ray et al. | |
| 8,269,950 B2* | 9/2012 | Spinelli | G01N 21/538 |
| | | | 356/4.01 |
| 8,338,785 B2 | 12/2012 | Ray | |
| 8,406,859 B2 | 3/2013 | Zuzak et al. | |
| 9,041,926 B2* | 5/2015 | Ray | G01S 17/95 |
| | | | 356/342 |
| 9,086,488 B2* | 7/2015 | Tchoryk, Jr. | G01S 17/95 |
| 9,116,243 B1* | 8/2015 | Brown | G01S 17/95 |
| 2011/0019188 A1 | 1/2011 | Ray et al. | |
| 2011/0058167 A1* | 3/2011 | Knox | G01N 15/06 |
| | | | 356/338 |
| 2014/0379263 A1* | 12/2014 | Ray | G01S 17/95 |
| | | | 702/3 |
| 2015/0146191 A1* | 5/2015 | Kotake | G01S 17/42 |
| | | | 356/28.5 |
| 2017/0268993 A1* | 9/2017 | Anderson | G01N 21/21 |

OTHER PUBLICATIONS

Extended European Search Report, for European Patent Application No. 18152500.7, dated Jul. 9, 2018, 11 pages.

* cited by examiner

CONTROLLED SAMPLING VOLUME OF CLOUDS FOR MEASURING CLOUD PARAMETERS

CROSS-REFERENCE TO RELATED APPLICATION(S)

This application is a continuation of U.S. application Ser. No. 15/411,548 filed Jan. 20, 2017 for "CONTROLLED SAMPLING VOLUME OF CLOUDS FOR MEASURING CLOUD PARAMETERS" by Mark Ray and Kaare Josef Anderson, which is incorporated by reference in its entirety.

BACKGROUND

Various cloud conditions can present risks to aircraft when traveling through them. If the temperature of a cloud atmosphere is below the freezing point for water, water droplets can become super-cooled liquid droplets. These super-cooled liquid droplets can then undergo a liquid-to-solid phase change upon impact with an aircraft surface. Ice accretes at different surface regions for different sizes of the super-cooled liquid droplets in the cloud atmosphere. Thus, characterizing the sizes of super-cooled water droplets in a cloud atmosphere can facilitate prediction of surface regions where ice will accrete as well as providing alerts of potentially dangerous conditions to a pilot.

Super-cooled small water droplets tend to form ice only on leading edges of an aircraft's exterior surface. Super-cooled Large water Droplets (SLDs), however, can strike the leading edge of a wing and run back past the icing protection systems, or can traverse airflow vectors and strike surfaces aft of these leading edges. Ice that forms on unprotected surface regions can severely alter the aerodynamics of the aircraft. Such ice accretion may cause aircraft stall or result in unpredictable aircraft control variation that might lead to flight issues. When in a cloud, ice can form on control surfaces and/or lift surfaces.

Not every cloud, however, has a significant SLD population. Different clouds and different atmospheric conditions may be accompanied by various water droplet size distributions, different ice/liquid ratios, etc., some of which may be entirely safe to an aircraft, while others may not be safe. Such water droplet size distributions and ice/liquid ratios may be measured as cloud metrics using various types of instruments.

Some aircraft are equipped with Light Detection and Ranging (LIDAR) systems to measure cloud metrics. Such systems can characterize clouds that have water droplets that have a size distribution having a single mode. Either the mean droplet size or the mode droplet size can be calculated by inversion of a backscatter signal using such systems. These systems can also calculate the density of water droplets for such mono-modal distributions.

Multi-modal distributions of water droplet sizes, however, can be difficult to characterize. Such multi-modal distributions may occur, for example, when cumulus clouds drop drizzle or rain into a lower stratiform cloud deck, creating icing conditions. For droplet size distributions having a dominant mode and a secondary mode (e.g. large distribution of relatively small water droplets plus a small distribution of large water droplets), it can be difficult to detect the anomalous amounts of large water droplets in the secondary mode.

LIDAR systems project pulses of a collimated laser beam into the cloud atmosphere and then sense the signal backscattered by the cloud atmosphere. The collimated laser beam samples a relatively small volume of the cloud, due to the collimated beam having a small field of view (e.g., 4 mrad of divergence is not atypical). Sampling such a small cloud volume can result in the beam encountering few, if any of the SLDs of a secondary distribution.

Depending on the size and density of the SLDs in the secondary distribution, the backscatter signal can appear as scintillation spikes superimposed on an otherwise smooth continuous range-resolved backscatter signal characteristic of the primary distribution. The size and frequency of occurrence of the scintillation spikes depends on the sizes of the SLDs and on the volume of space probed by the collimated laser beam.

Unlike the smooth range-resolved backscatter signal from the primary distribution, backscatter signals from small distributions of large droplet can have randomly occurring scintillation spikes. Averaging of such backscatter signals over multiple laser pulses, while boosting the signal-to-noise ratio of the sparse droplet contribution, can cause the sporadic scintillation spikes for the sparse large droplet distribution to be attenuated, and perhaps even fall below a noise floor. Thus, the SLDs, which can be hazardous to aircraft, may not be sensed.

Mono-modal distributions of SLDs can also be problematic. Again, if the density of SLDs is small, the backscatter signal can be characterized by scintillation spikes randomly located in the temporal stream of backscatter signals. Averaging of such backscatter signals can result in a signal amplitude that is small. Such a small signal may even fall below an instrument noise floor. Measurement techniques and instruments, which can more accurately characterize water droplet distributions, are needed.

SUMMARY

Apparatus and associated methods relate to a system for calculating a metric of Super-cooled Large Droplets (SLDs) in a cloud atmosphere. The system includes an optical source configured to divergently project first and second pulses of optical energy about an optical axis. The system includes an optical control module configured to receive at least a portion of each of the first and second divergently projected pulses of optical energy and to direct the received portion of each of the first and second divergently projected pulses within a projection range. The system includes a collimator lens located within the projection range of the optical control module and configured to collimate a portion of each of the first and second pulses of optical energy directed by the optical control module therethrough into a cloud atmosphere. The system includes an optical window located within the projection range of the optical control module and configured to transmit an uncollimated portion of each of the first and second pulses of optical energy directed by the optical control module therethrough into a cloud atmosphere. The system includes an optical detector configured to detect and to generate first and second signals indicative of each of the first and second pulses of optical energy, respectively, backscattered by the cloud atmosphere. A difference between a first ratio and a second ratio of the collimated to the uncollimated portions corresponding to each of the first and second pulses of optical energy is greater than 0.10. The system also includes a processor configured to calculate, based on the generated first and second signals, a metric of SLDs in the cloud atmosphere.

Some embodiments relate to a method for calculating a metric of Super-cooled Large Droplets (SLDs) in a cloud atmosphere. The method includes generating first and second pulses of optical energy. The method includes divergently projecting the generated first and second pulses of optical energy over a solid angle greater than a predetermined threshold. The method includes redirecting at least a portion of each of the first and second divergently projected pulses of optical energy within a projection range. The method includes collimating a portion of the redirected first and/or second divergently projected pulses into a first projection volume of a cloud atmosphere. The method includes transmitting an uncollimated portion of the divergent first and/or second divergently projected pulses of optical energy into a second projection volume of the cloud atmosphere. The method includes detecting and generating first and second signals indicative of each of the first and second pulses of optical energy, respectively, backscattered by the cloud atmosphere. A difference between a first ratio and a second ratio of the collimated to the uncollimated portions corresponds to each of the first and second pulses of optical energy is greater than 0.10. The method also includes calculating, based on first and second generated signals, a metric of SLDs in the cloud atmosphere.

DETAILED DESCRIPTION

Apparatus and associated methods relate to determining a size and/or density of Super-cooled Large Droplets (SLDs) in a cloud atmosphere by comparing detected optical signals reflected from small and large sampling volumes of a cloud atmosphere. In some embodiments, an optical pulse is generated and divergently projected from a first optical fiber. A collimating lens is aligned within the divergently projected optical pulse collimating a portion thereof. The collimated and uncollimated portions of the optical pulse are projected into the small and large sampling volumes of the cloud atmosphere, respectively. The ratio of the collimated to the uncollimated portions can be optically controlled. Signals corresponding to optical pulses having different collimated/uncollimated ratios are backscattered by the cloud atmosphere, detected and compared to one another. A processor is configured to calculate, based on scintillation spike differences between the optical pulses of different collimated/uncollimated ratios, a size and/or density of SLDs.

Apparatus and associated methods relate to sampling both large and small volumes of a cloud atmosphere. Sampling a large volume of a cloud atmosphere facilitates obtaining a large signal response from even a sparse distribution of water droplets in the cloud atmosphere. Such a large volume can be probed by projecting an uncollimated optical beam into the cloud atmosphere and sampling the signal backscattered from the water droplets located within the probed volume. Sampling a small volume of a cloud atmosphere complements the large volume sampling and facilitates quantization of various metrics of the cloud atmosphere. A small volume can be probed by projecting a collimated optical beam into the cloud atmosphere.

The uncollimated optical beam can be generated by projecting a pulse of light energy from an end of a first optical fiber. The pulse of light energy can be projected from a polished surface of the first optical fiber, for example, without having a lens between the end of the optical fiber and the cloud atmosphere. The unlensed beam can diverge as it projects from the end of the first optical fiber. Various metrics can be used to characterize the divergence of the projected optical beam. For example, angle of divergence ($\theta$), numerical aperture (NA), focal ratio (F/#), and solid angle ($\Omega$) can all be used as metrics characterizing the divergence of the projected optical beam.

Figure 1:
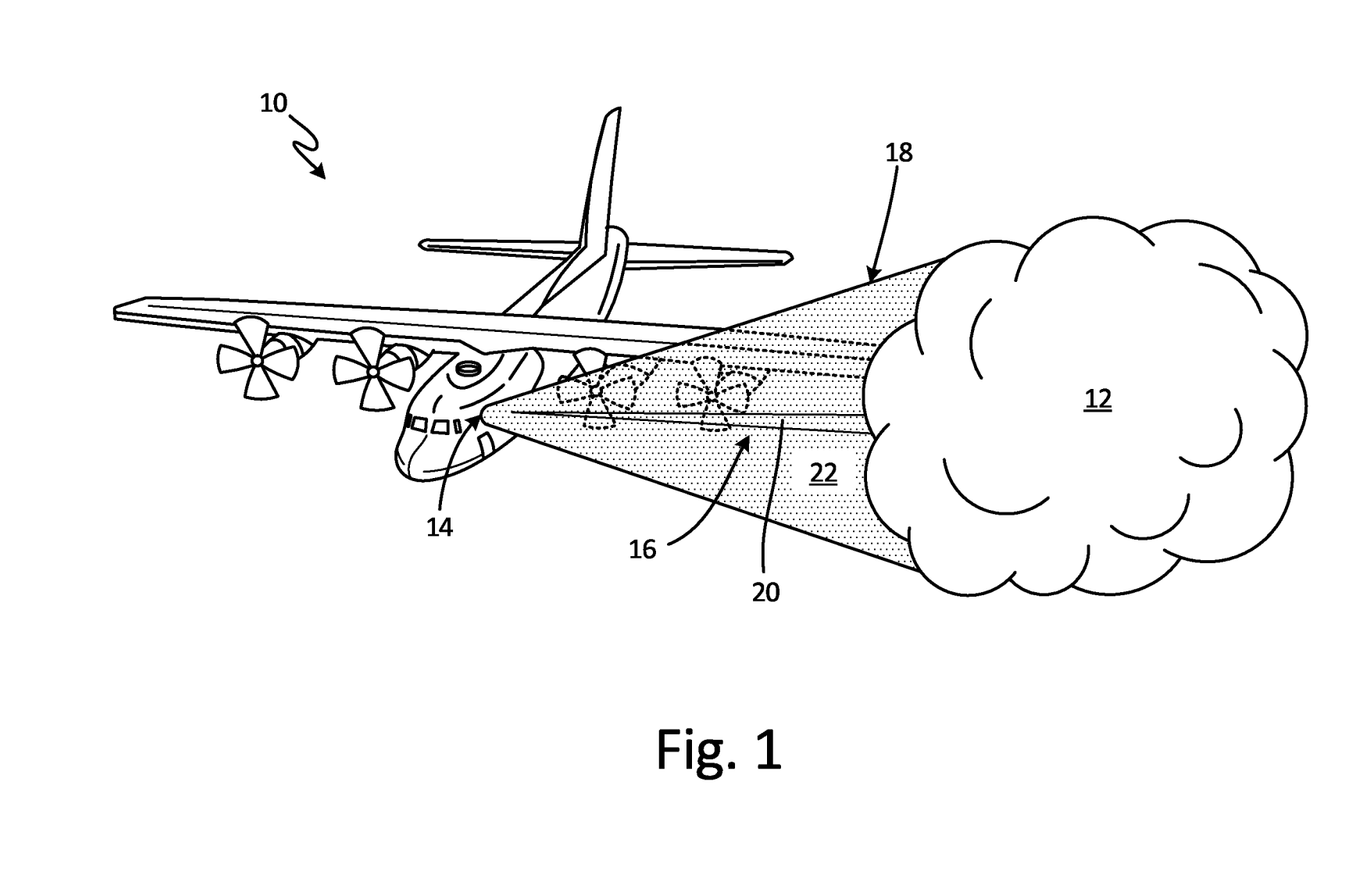
FIG. 1 is a schematic view of an aircraft using an exemplary cloud conditions measurement system using both a collimated portion and an uncollimated portion of pulses of optical energy.

FIG. 1 is a schematic view of an aircraft using an exemplary cloud conditions measurement system using both a collimated portion and an uncollimated portion of each pulse of optical energy. In FIG. 1, aircraft 10 is traveling through cloud atmosphere 12. Aircraft 10 is equipped with cloud conditions measurement system 14 that is probing cloud atmosphere 12 with collimated portion 16 and uncollimated portion 18 of each pulse of optical energy.

Collimated portion 16 of each pulse of optical energy has a relatively small divergence and is projected into first projection volume 20 of cloud atmosphere 12. In some embodiments, the divergence of collimated portion 16 can be characterized by an angle of divergence of 4 mrad, for example. An exemplary cloud atmosphere, which is sampled over a depth of ten meters by such a collimated optical beam, results in a first probe volume 20 being equal to about $5 \times 10^{-3} m^3$.

Uncollimated portion 18 has a relatively large divergence and is projected into second projection volume 22. In some embodiments, the divergence of uncollimated portion 18 can be a result of projection from an optical fiber having a numerical aperture of 0.39, for example. An exemplary cloud atmosphere, which is sampled over a depth of ten meters by such an uncollimated optical beam results in second probe volume 22 being equal to about $170 m^3$. Thus, second probe volume 22 is more than thirty-thousand times larger than first probe volume 20.

Each of the collimated and uncollimated portions 16 and 18 can be backscattered by water droplets and ice crystals of cloud atmosphere 12. The optical energy backscattered by cloud atmosphere 12 can be detected by one or more optical detectors. The detector can then generate electrical signals corresponding to the detected optical energy so backscattered by cloud atmosphere 12. The generated electrical signals are indicative of various metrics of cloud atmosphere 12.

If only the uncollimated portion of the optical energy beam is projected into and backscattered by cloud atmosphere 12, a relatively large volume of cloud atmosphere 12 from which water droplets backscatter the pulses of optical energy is sampled. This large volume is likely to have water particles distributed fairly uniformly throughout the sampled volume. Even should the particle density be relatively modest, such a large sample volume would likely have many particles well distributed throughout the range distances from the optical source. When large volumes of cloud atmosphere 12 are sampled using such an uncollimated LIDAR system, backscattering results from a great many water droplets, which are encountered at many range locations from the location where the pulses of optical energy are emitted. The corresponding backscatter signal that is generated when sampling such a large volume will be a smooth continuous range-resolved backscatter signal, with the range corresponding to photonic round-trip flight time (e.g., time for light to travel from an optical source to a backscattering water droplet within the sampling volume, plus the return time to an optical detector).

If, however, only the collimated portion of the optical energy beam were projected into and backscattered by cloud atmosphere 12, a relatively small volume of cloud atmosphere 12 is sampled. When small volumes of cloud atmosphere 12 are sampled using such a collimated LIDAR system, backscattering results from the relatively rare photonic encounter with a water droplet. Each backscattering event is encountered at a specific range location from the location where the pulses of optical energy are emitted. The corresponding backscatter signal that will be generated when sampling such a small volume will be a series of scintillation spikes generated at each photonic round-trip flight time.

In such small-sample-volume scenarios, the generated signal indicative of various cloud metrics can be marked with scintillation spikes, each corresponding to a photonic round trip flight time to and from a particular water droplet. Even when probing small sample volumes, many, if not most, clouds have so many small droplets distributed throughout the sampling volume that the generated backscatter signal is relatively smooth and continuous. Scintillation spikes usually result from Super-cooled Large Droplets (SLDs). SLDs are often found in clouds having a bimodal distribution, with the primary mode including small droplets. In such bimodal cloud scenarios, the signal detected when sampling small volumes of bimodally-distributed water droplets can have scintillation spikes superimposed upon a smooth continuous range-resolved backscatter signal. The scintillation spike portion of the backscatter signal principally results from SLD backscattering, while the smooth continuous portion of the backscatter signal results from backscattering from small but densely-distributed droplets.

Thus, obtaining signals facilitating the isolation of both the smooth continuous and the scintillation-spike portions of the backscatter signal can facilitate determination of metrics of both the primary-mode droplets and the secondary-mode droplets.

Figures 2A, 2B:
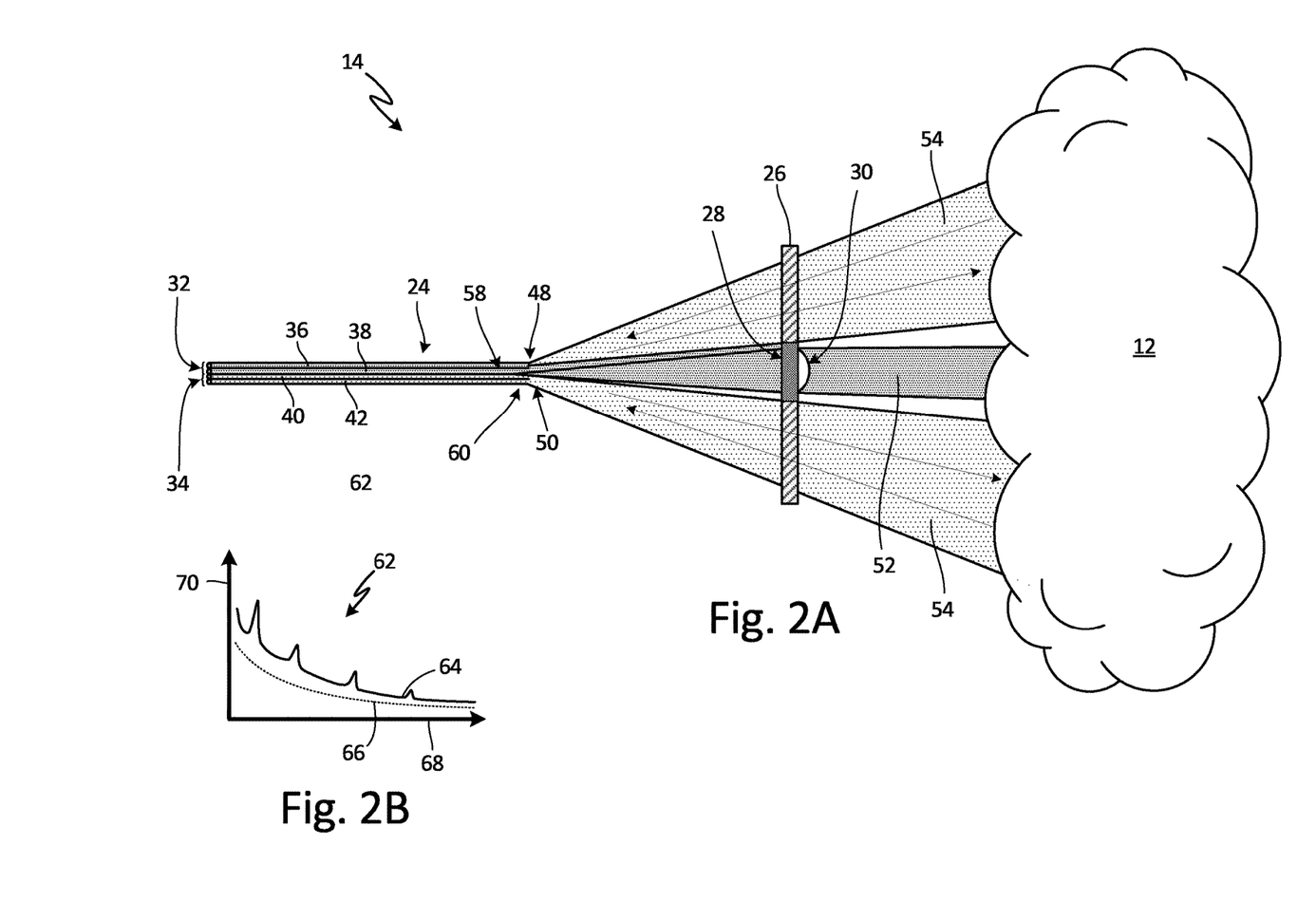
FIG. 2A is a schematic diagram of an embodiment of a cloud conditions measurement system generating both collimated and uncollimated portions of a light beam.
FIG. 2B is a graph of exemplary backscatter signals resulting from both collimated and uncollimated portions of a light beam.

FIG. 2A is a schematic diagram of an embodiment of a cloud conditions measurement system that generates both collimated and uncollimated portions of pulses of optical energy (e.g., light beams). In FIG. 2A, cloud conditions measurement system 14 is depicted probing cloud atmosphere 12. Cloud conditions measurement system 14 includes fiber bundle 24, window 26, optical filter 28, and collimating lens 30. In the depicted embodiment, fiber bundle 24 includes two transmitter/receiver pairs 32 and 34 of fibers. First transmitter/receiver pair 32 can be configured to transmit, via first transmitter fiber 36, and receive, via first receiver fiber 38, optical energy of a first wavelength, for example. Second transmitter/receiver pair 34 can be configured to transmit, via second transmitter fiber 40, and receive, via second receiver fiber 42, optical energy of a second wavelength.

Pulses of optical energy are generated by an optical source (not depicted) and transmitted via first and/or second transmitter fibers 36 and 40 and divergently projected from transmitter ends 48 and 50, respectively. Measures of divergence of the divergently projected pulses of optical energy can be determined by a numerical aperture (NA) of the projection ends 48 and 50. In some embodiments, the NA of the projection ends 48 and 50 are substantially equal to one another. In some embodiments the NA of the projection ends 48 and 50 are dissimilar from one another.

Window 26 is aligned with the divergently projected pulses of optical energy. Filter 28 is aligned with a center region of window 26 in the depicted embodiment. Filter 28 is depicted as transmitting a centrally-projected portion of divergently projected pulses of optical energy of the first wavelength and absorbing a centrally-projected portion of divergently projected pulses of optical energy of the second wavelength. In some embodiments, filter 28 is a bandpass filter that, for example, transmits optical energy of the first wavelength and absorbs optical energy of a second wavelength. In some embodiments, transmission and absorption of optical pulses can be controlled in other ways. For example, a shutter can be controlled to pass or block pulses projected at different times. In some examples, LCD technology can provide electrical control of light absorption.

Collimating lens 30 is aligned with a center region of window 26 and with filter 28 in the depicted embodiment. Collimating lens 30 is depicted as collimating the centrally-projected portion of divergently projected pulses of optical energy of the first wavelength and directing the collimated portion into a fist projection volume 52 of cloud atmosphere 12. Portions not collimated by collimating lens 30 of divergently projected pulses of optical energy of the first wavelength are projected into a second projection volume 54 of cloud atmosphere 12. Similarly portions not absorbed by filter 28 of divergently projected pulses of optical energy of the second wavelength are projected into third projection volume (e.g., third projection volume is approximately the same as second projection volume 54) of cloud atmosphere 12.

The portions of pulses of optical energy projected into each of the projection volumes 52 and 54 can be backscattered by cloud atmosphere 12. The collimated portion of each of the optical energy pulses of the first wavelength projected into first projection volume 52 can be approximately ray-traced back upon its projection path and then focused by collimating lens 30 onto receiver end 58 of receiver fiber 38. The uncollimated portion of each of the optical energy pulses of the first wavelength projected into second projection volume 54 can be approximately ray-traced back upon its projection path and is also received by receiver end 58 of receiver fiber 38. Similarly, the uncollimated portions of optical energy pulses of the second wavelength projected into third projection volume can be approximately ray-traced back upon its projection path and is received by receiver end 60 of receiver fiber 42.

Both collimated and uncollimated portions of the pulses of optical energy are received and subsequently detected by an optical detector (not depicted). The uncollimated portions are projected into projection volume 54, which is comparatively large with respect to projection volume 52 into which the collimated portion is projected. The relatively large sampling volume (i.e., the portion of the projection volume that contributes to a detectable signal of the projected optical energy backscattered by the cloud atmosphere) ensures that virtually all of the droplets in the cloud, small or large, are illuminated, and from which photons are backscattered and subsequently detected. Sampling such a large number of droplets results in a smooth, continuous range-resolved backscatter signal. Even should the cloud have a bimodal distribution of droplet sizes, the contribution of large droplets may still be too small to result in a backscatter signal that can be differentiated from one caused by a monomodal small-droplet cloud.

Conversely, the collimated portion is projected into projection volume 52, which is comparatively small; with respect to projection volume 54 onto which the uncollimated portions are projected. The relatively small sampling volume ensures that a relatively modest number of droplets in the cloud, small or large, are illuminated and their backscatter detected. Sampling such a small number of droplets results in a scintillation spikes superimposed on an otherwise smooth, continuous, range-resolved backscatter signal. A cloud that has a bimodal distribution of droplet sizes can thereby be differentiated, via the scintillation spikes, from a monomodal small-droplet cloud.

FIG. 2B is a graph of exemplary backscatter signals resulting from both collimated and uncollimated portions of a light beam. In FIG. 2B, graph 62 includes two range-resolved backscatter signals 64, 66. First range-resolved backscatter signal 64 corresponds to a projected pulse of optical energy having both collimated and uncollimated portions. Second range-resolved backscatter signal 66 corresponds to a projected pulse of optical energy having only an uncollimated portion. Graph 62 has horizontal axis 68, which is indicative of range within cloud atmosphere 12 from which the projected optical energy is backscattered. Graph 62 has vertical axis 70, which is indicative of intensity of the detected backscatter signal. Note that backscatter signal 64 includes scintillation spikes corresponding to the collimated portions of the projected pulses of optical energy. Note also that backscatter signal 66 has no scintillation spikes due to the absence of signal contribution corresponding to a collimated sampling volume.

Some embodiments include a processor to receive backscatter signals 64 and 66. The processor can be configured to calculate, based on the received backscatter signals 64 and 66, metrics of cloud atmosphere 12. The processor can be configured, for example, to calculate a density and or an average size of SLDs in the cloud atmosphere based on the smooth continuous backscatter signal 66. The processor can be configured to calculate a density and/or a size metric based on the scintillation spikes of backscatter signal 64. For example, in some embodiments, the size of a scintillation spike can be indicative of a size of a SLD. In some embodiments, a frequency and/or density of scintillation spikes along the horizontal axis time 112 (e.g., time or range) axis can be indicative of a density of SLDs. In some embodiments, processor can use both backscatter signals 64 and 66 to calculate metrics of a bimodal distribution of water droplets in cloud atmosphere 12.

Figure 3:
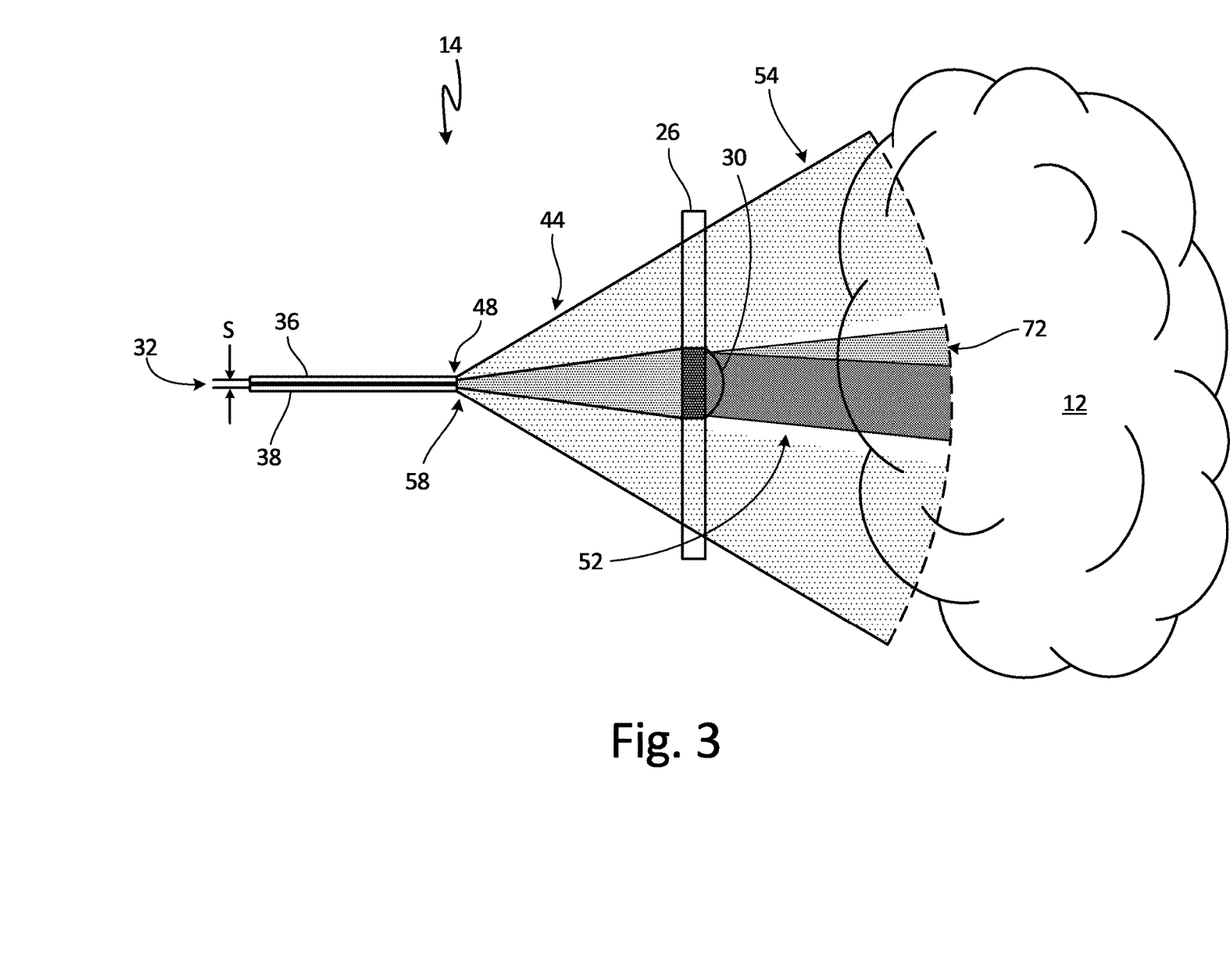
FIG. 3 is a schematic diagram that illustrates the relationship between the projected field of view and the received field of view for adjacent fibers sharing a common lens.

FIG. 3 is a schematic diagram that illustrates the relationship between the projector field of view and the receiver field of view for adjacent fibers sharing a common lens. In FIG. 3, cloud conditions measurement system 14 is depicted probing cloud atmosphere 12. Only first transmitter/receiver fiber pair 32 is depicted, so as to permit the collimated and uncollimated portions of divergent optical-energy pulses produced by a first optical source to be depicted unobscured by the uncollimated portion of each divergent optical-energy pulse (depicted in FIG. 2A) by a second optical source.

In FIG. 3, transmitter fiber 36 has transmitter end 48 is aligned proximate and substantially parallel to receiver end 58 of receiver fiber 38. Transmitter fiber 36 transmits pulses of optical energy and divergently projects the transmitted pulses from transmitter end 48. Each of the divergent pulses has two portions: i) a collimated portion projected into projection volume 52; and ii) an uncollimated portion projected into projection volume 54. The collimated portion is the portion of a divergent pulse of optical energy that is collimated by collimator lens 30. The uncollimated portion is the portion of a divergent pulse of optical energy that is not collimated by collimator lens 30. In this way, both the collimated and the uncollimated portions are complementary to one to another.

The collimated portion is projected by collimator lens 30 into first projection volume 52. The uncollimated portion is divergently projected by transmitter end 48, through window 26, and into cloud atmosphere 12. Because transmitter end 48 and receiver end 58 are adjacent to one another, albeit close to one another, first reception volume 72 of cloud atmosphere from which light is focused on receiver end 58 is not exactly the same volume as first projection volume 52. First reception volume 72 corresponds to the field of view of receiver end 58 or receiver fiber 38 as imaged by collimator lens 30. At range locations that are nearby or close to collimator lens 30, first projection volume is substantially coextensive with first reception volume 72. But as the range location becomes more distal from collimator lens, first projection volume 52 and first reception volume 72 diverge from one another. At a specific range location, the intersection between first projection volume 52 and first reception volume 72 becomes non-existent.

Such a range at which the intersection of first projection volume 52 and first reception volume 72 becomes zero can be mathematically determined. Using a spherical collimating lens 30 and assuming that the collimated portions of projected optical energy pulses are well-collimated with approximately no divergence, the separation is approximately:

$$R = (L-S)\left(\frac{f}{s-d}\right)$$

Here, R is the calculated range at which no intersection of first projection volume 52 and first reception volume 72 begins. L is the diameter and f is the focal length of collimating lens 30. S is center-to-center separation between transmitter and receiver ends 48 and 58 of transmitter and receiver fibers 36 and 38, respectively. And d is the diameter of the transmitter and receiver fibers 36 and 38. For example, if L=6 mm, f=25 mm, S=300 μm, and d=250 μm, then R is calculated to be 2.85 meters.

For some cloud atmospheres, such a small range can result in too few Super-cooled Large Droplets to be distributed therein for adequate measurement. For such cloud atmospheres, sampling volumes that are larger than the above calculated one, and yet smaller than sampling volumes 54 and 56 can be desirable for use in determining metrics of SLDs.

Figure 4A:
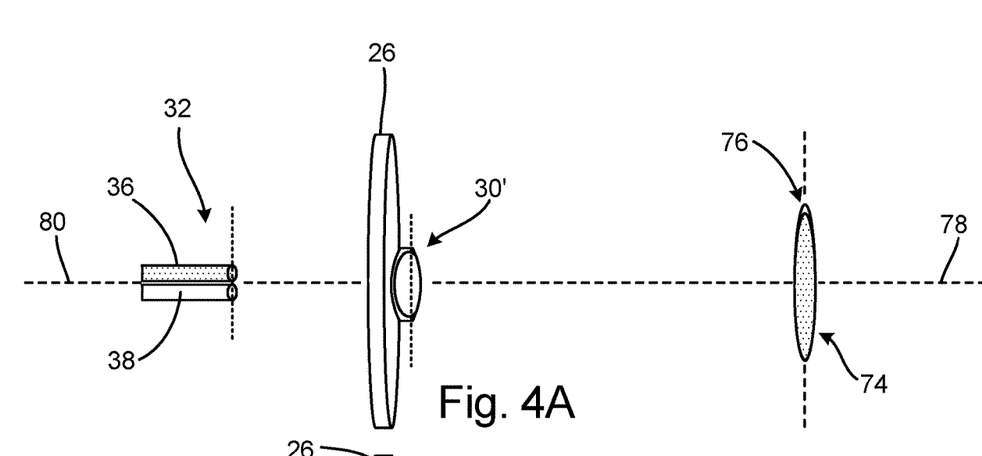
FIGS. 4A-4B are schematic diagrams that illustrate the relationship between the sampling volume and the relative orientation between a cylindrical lens and transmitter/receiver fiber orientation.
Figure 4B:
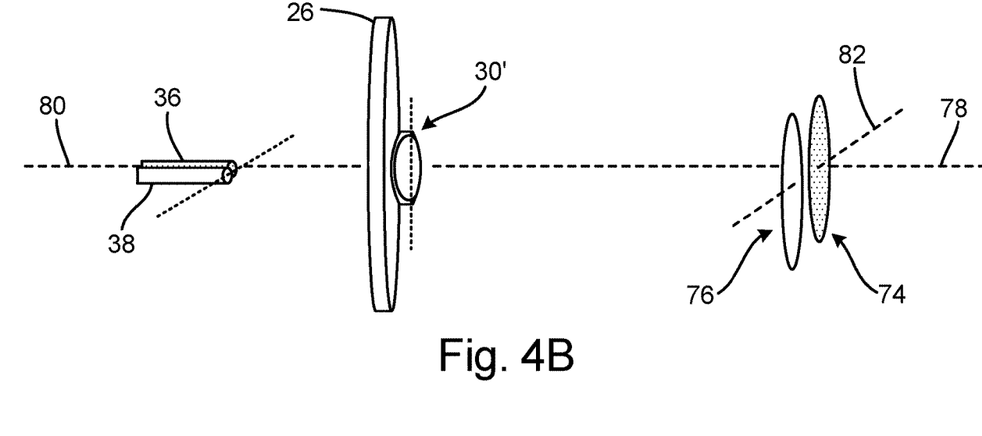

FIGS. 4A-4B are schematic diagrams that illustrate the relationship between the sampling volume and the relative orientation between a cylindrical lens and transmitter/receiver fiber orientation. In FIGS. 4A-4B, window 26, instead of having a spherical collimating lens, has a cylindrical collimating lens 30'. In FIGS. 4A-4B, transmitter/receiver fiber pair 32 is axially aligned with window 26, cylindrical collimating lens 30', and projected fields of view 74 and 76 along central axis 78. Projected field of view 74 corresponds to transmitter fiber 36 of transmitter/receiver fiber pair 32. Projected field of view 76 corresponds to receiver fiber 38 of transmitter/receiver fiber pair 32. Projected fields of view 74 and 76 are elliptical instead of spherical, because collimating lens 30' is cylindrical instead of spherical. Cylindrical collimating lens 30' has high curvature in a transverse direction and low curvature in a longitudinal direction. Such astigmatic curvature causes the elliptical fields of view 74 and 76 to have a long extent in the longitudinal direction and a short extent in the transverse direction.

In FIG. 4A, projected fields of view 74 and 76 are displaced from one another along longitudinal axis 80, which is caused by the separation distance S between transmitter fiber 36 and receiver fiber 38. Because transmitter fiber 36 and receiver fiber 38 are separated in a direction parallel to longitudinal axis 80, fields of view 74 and 76 are also displaced from one another along the longitudinal axis 80. Because the fields of view 74 and 76 are relatively extensive in the longitudinal direction, the intersection of the transmitter and receiver fields of view 74 and 76 is large (e.g., much greater than 50% of each field of view).

In FIG. 4B, transmitter and receiver fibers 36 and 38 are rotated with respect to optical axis 78. Transmitter and receiver fibers 36 and 38 are aligned parallel to transverse axis 82 in FIG. 4B. Transverse axis 82 is orthogonal to both optical axis 78 and longitudinal axis 80. Because the separation between transmitter and receiver fibers 36 and 38 is in a direction parallel to transverse axis 82 (e.g., in a transverse direction), fields of view 74 and 76 are displaced one from another along transverse axis 82. In the depicted schematic, fields of view 74 and 76 are displaced such that no intersection remains between fields of view 74 and 76. Thus, the intersection between fields of view 74 and 76 is a function of the relative orientation of the transmitter/receiver fiber pair 32 and orientation of cylindrical collimating lens 30'.

The fields of view of the uncollimated portions corresponding to transmitter and receiver optical fibers 36 and 38 are much larger than for the collimated portions. Because the fields of view of the uncollimated portions are quite large, alignment of transmitter/receiver fibers 36 and 38 is not as important as for the collimated portions. Uncollimated portions corresponding to transmitter and receiver optical fibers 36 and 38 can be substantially equal or substantially the same so that the volume of the cloud atmosphere probed by a signal projecting from the first optical fiber is substantially the same volume from which a backscattered signal is received by the second optical fiber. Two fields of view, and any of the measures of divergence that characterize such fields of view, are substantially equal to one another if they differ by less than ten percent. For example if $2(\theta_2-\theta_1)/(\theta_2+\theta_1)<0.1$ then the two angles of divergence are substantially equal to each other.

Figure 5:
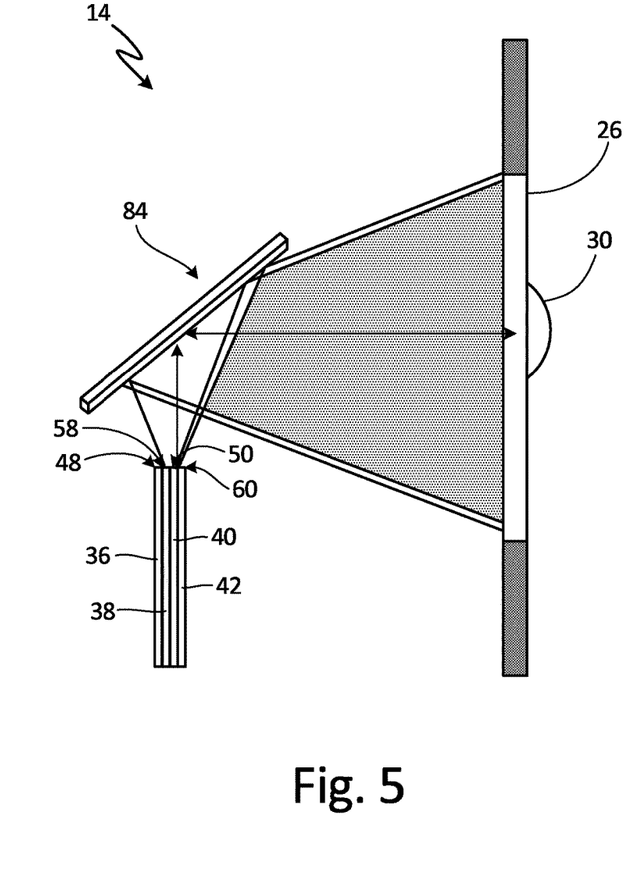
FIG. 5 is a schematic diagram of a cloud conditions measurement system that has a Digital Micro-mirror Device (DMD) for directing pulses of optical energy into or away from a collimator lens.

FIG. 5 is a schematic diagram of a cloud conditions measurement system that has a Digital Micro-mirror Device (DMD) for directing pulses of optical energy into or away from a collimator lens. In FIG. 5, cloud conditions measurement system 14 includes DMD 84 interposed between ends 48, 50, 58 and 60 of optical fibers 36, 38, 40 and 42, respectively, and optical window 26 with collimator lens 30. DMD is a two-dimensional array of mirrors of DMD 84 that are pivotable from a nominal position. DMD is depicted with every element of the two-dimensional array in its nominal position. In such a position, the two-dimensional array acts as a unitary mirror, receiving divergently projected pulses of optical energy and directing them through window 26 and collimator lens 30.

Because each of the elements of two-dimensional array of the pivotable mirrors of DMD 84 are pivotable, received pulses of optical energy can be directed in other directions. For example, received pulses of optical energy can be directed so as to avoid collimator lens 30, for example, or received pulses of optical energy can be directed to avoid window 26. In some embodiments, only certain portions of received pulses of optical energy can be directed so as to avoid window 26 and/or window 30.

Figure 6A:
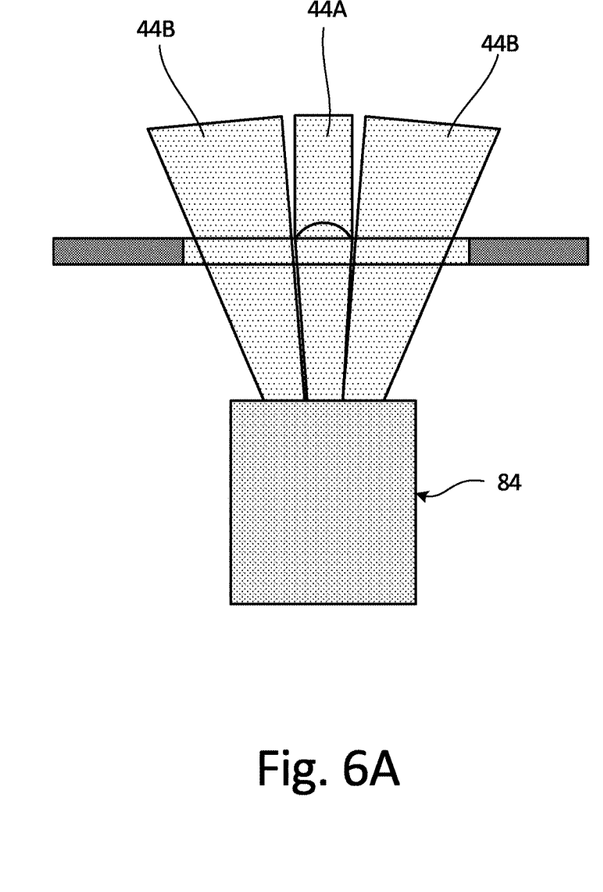
FIG. 6A is a schematic diagram showing collimated and uncollimated portions of a projected pulse of optical energy directed by a DMD.

FIG. 6A is a schematic diagram showing collimated and uncollimated portions of a projected pulse of optical energy directed by a DMD. In FIG. 6A, cloud conditions measurement system 14 is shown from a plan view perspective with respect to the perspective depicted in FIG. 5. A first pulse of optical energy is depicted, so as to permit the collimated and uncollimated portions of the divergent optical-energy pulse produced by a first optical source to be depicted unobscured by the uncollimated portion of second divergent optical-energy pulse produced by a second optical source. DMD 84 reflects both first portion 44A (e.g. a portion that will be collimated) and second portion 44B (e.g., a portion that will remain uncollimated) of the pulse of optical energy. Collimated portion 44A is directed by DMD 84 through collimator lens 30. Uncollimated portion 44B of the pulse of optical energy is directed by DMD 84 through window 26.

Figure 6B:
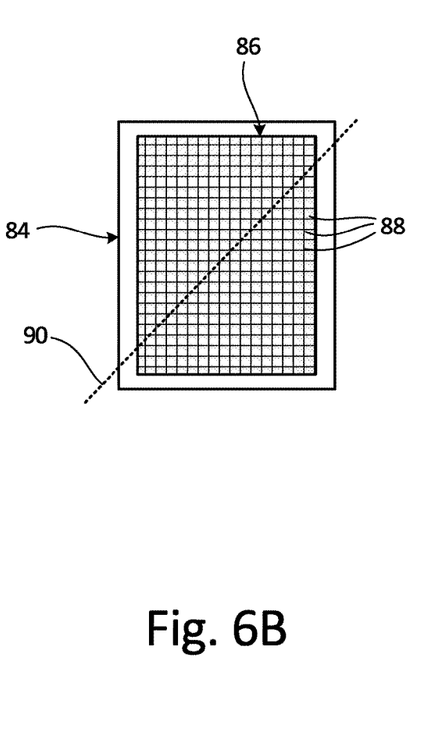
FIG. 6B discloses an exemplary DMD having a two-dimensional array of pivotable mirrors.

DMD directs both collimated portion 44A and uncollimated portion 44B through collimator lens 30 and window 26, respectively when each of the pivotable mirrors of DMD 84 is in a nominal pivot position. FIG. 6B discloses an exemplary DMD having a two-dimensional array of pivotable mirrors. DMD 84 discloses two-dimensional array 86 of mirrors 88, each pivotable about a nominal pivot position. Each of pivotable mirrors 88 pivot about an axis that is parallel to micro-mirror tilt axis 90. Each of pivotable mirrors 88 pivots in response to an electrical control signal. Each of pivotable mirrors 88 can be independently pivoted, so as to create a controlled two-dimensional reflection profile.

In some embodiments DMD 84 is configured to operate in a first mode for the first pulse of optical energy and in a second mode for the second pulse of optical energy. In the first mode, at least a portion of a pulse of optical energy is directed through the collimator lens 30 thereby being collimated. In the first mode, a first ratio of collimated portion 44A to uncollimated portion 44B can be calculated. In the second mode, DMD 84 can be configured to direct little or no optical energy of second pulse of optical energy 46 through collimator lens 30. In the second mode, a first ratio of collimated portion 44A to uncollimated portion 44B can be determined. If no energy is directed through collimator lens 30, such a calculated ratio will be zero. If, however, little or no energy is directed through window 26, such a calculated ratio will be infinite.

Figure 7A:
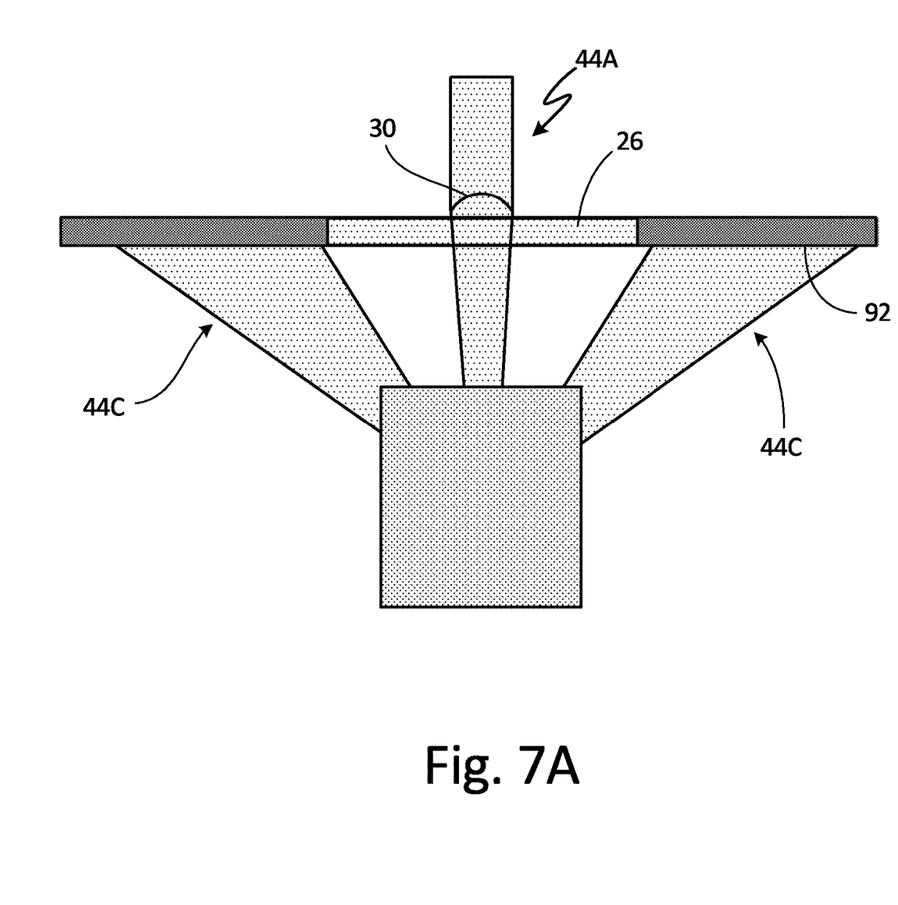
FIG. 7A is a schematic diagram showing a DMD directing a pulse of optical energy through a collimator lens.

FIG. 7A is a schematic diagram showing a DMD directing a pulse of optical energy through a collimator lens. In FIG. 7A, DMD 84 is operating in the first mode as described above with reference to FIG. 6A. DMD 84 is directing a collimated portion 44A of first pulse 44 of optical energy through collimator lens 30. In the first mode of operation, DMD is also directing absorbed portion 44C of first pulse 44 of optical energy into an annular optical absorbing surface 92. In the depicted embodiment, DMD 84 is directing little or no optical energy through window 26. As a result, the calculated ratio of optical energy of collimated portion 44A to uncollimated portion 44B (Depicted in FIG. 6A), is infinite.

Figure 7B:
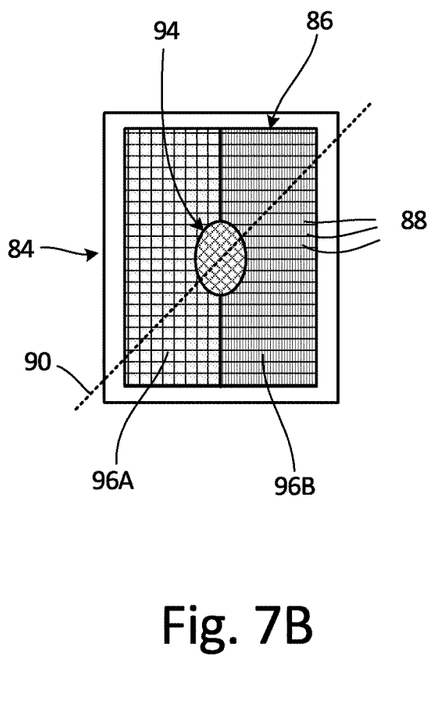
FIG. 7B discloses a two-dimensional array of pivotable mirrors of an exemplary DMD operating in a first mode.

FIG. 7B discloses a two-dimensional array of pivotable mirrors of an exemplary DMD operating in the first mode. In FIG. 7B, two-dimensional array 86 of pivotable mirrors 88 includes two regions 94 and 96 (region 96 is depicted as two sub-regions 96A and 96B). First region 94 includes pivotable mirrors 88 that are located in a central region of two-dimensional array 86. Second region 96A and 96B includes pivotable mirrors 88 that located on the periphery of two-dimensional optical array 86 circumscribing first region 94. Pivotable mirrors 88 located within first region 94 are configured to direct collimated portion 44A of first pulse 44 of optical energy through collimator lens 26. Pivotable mirrors 88 located within second region 96A and 96B are configured to direct absorbed portion 44C of first pulse 44 of optical energy to optical absorbing surface 92.

Figure 8A:
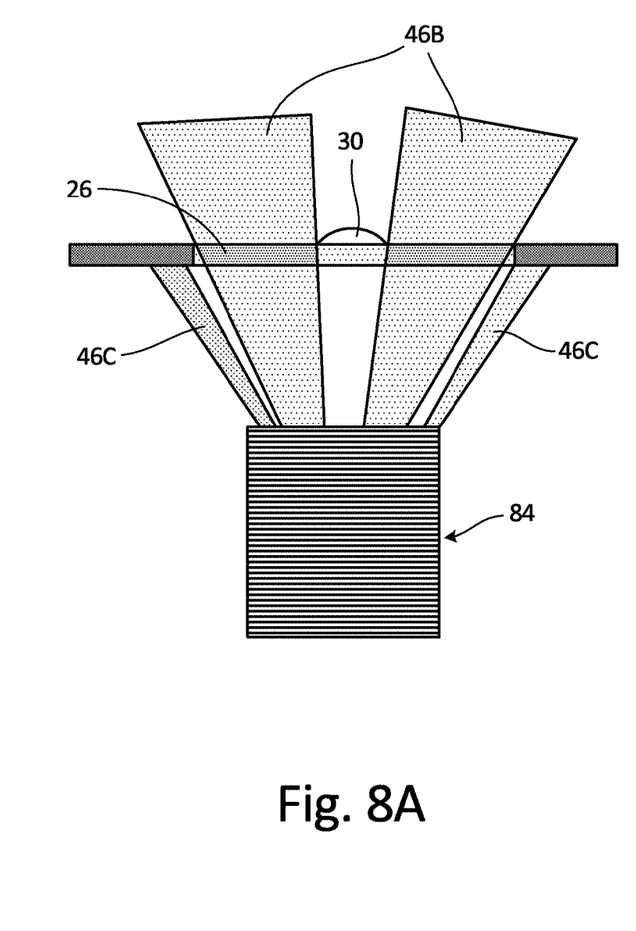
FIG. 8A is a schematic diagram showing a DMD directing a pulse of optical energy through a window.

FIG. 8A is a schematic diagram showing a DMD directing a pulse of optical energy through a window. In FIG. 8A, DMD 84 is operating in the second mode as described above with reference to FIG. 6A. DMD 84 is directing an uncollimated portion 46B of second pulse 46 of optical energy through window 26. In the first mode of operation, DMD is also directing absorbed portion 46C of second pulse 46 of optical energy into an annular optical absorbing surface 92. In the depicted embodiment, DMD 84 is directing little or no optical energy through collimator lens 26. As a result, the calculated ratio of optical energy of collimated portion 46A (Depicted in FIG. 6A) to uncollimated portion 46B is zero.

Figure 8B:
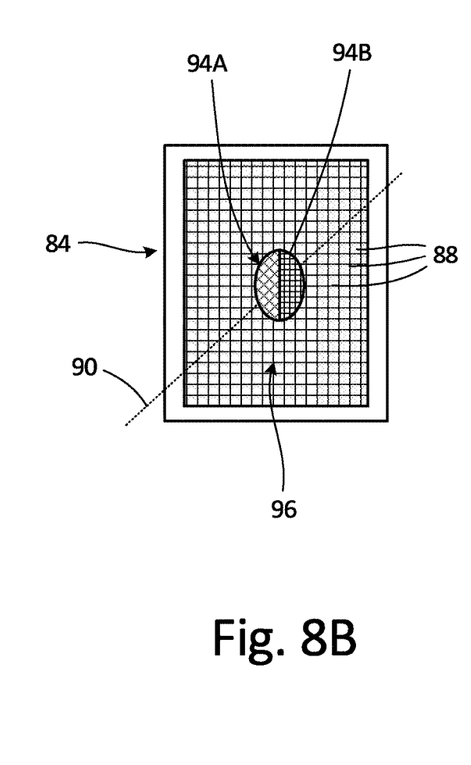
FIG. 8B discloses a two-dimensional array of pivotable mirrors of an exemplary DMD operating in a second mode.

FIG. 8B discloses a two-dimensional array of pivotable mirrors of an exemplary DMD operating in the second mode. In FIG. 7B, two-dimensional array 86 of pivotable mirrors 88 includes two regions 94 and 96 (region 94 is depicted as two sub-regions 94A and 94B). First region 94A and 94B includes pivotable mirrors 88 that are located in a central region of two-dimensional array 86. Second region 96 includes pivotable mirrors 88 that located on the periphery of two-dimensional optical array 86 circumscribing first region 94. Pivotable mirrors 88 located within first region 94 are configured to direct absorbing portion 46C of second pulse 46 of optical energy to optical absorbing surface 92. Pivotable mirrors 88 located within second region 96 are configured to direct uncollimated portion 44B of second pulse 46 of optical energy through window 30.

Figure 9A:
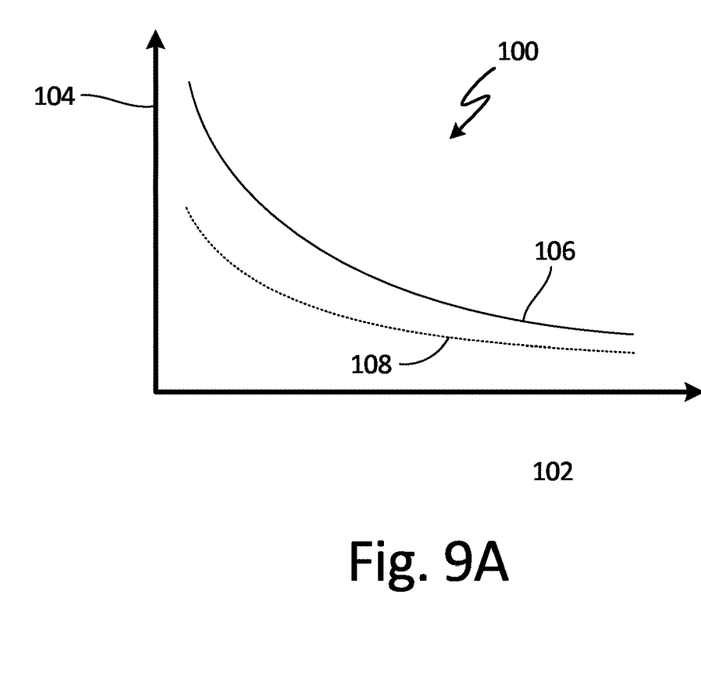
FIGS. 9A-9B depict exemplary backscatter signals corresponding to pulses of optical energy backscattered by a cloud atmosphere.
Figure 9B:
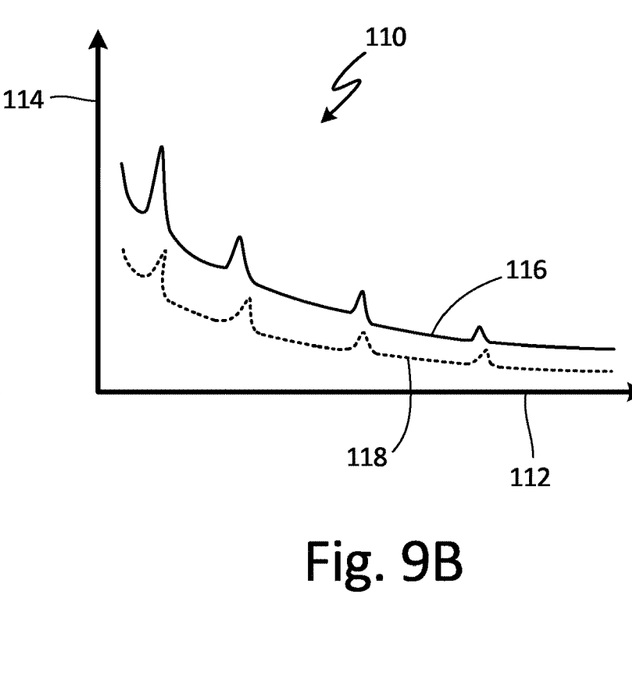

FIGS. 9A-9B depict exemplary backscatter signals corresponding to pulses of optical energy backscattered by a cloud atmosphere. In FIG. 9A, graphs 100 includes horizontal axis 102, vertical axis 104 and backscatter signals 106 and 108. Horizontal axis 102 represents time and/or range within a cloud atmosphere. Vertical axis 104 represents signal strength of backscatter signals 106 and 108 backscattered by the cloud atmosphere and detected by an optical detector. Backscatter signals 106 and 108 correspond to first and second pulses of optical energy 44 and 46, respectively. First pulse 44 of optical energy was generated by a first optical emitter having a first wavelength, and second pulse of optical energy was generated by a second optical emitter having a second wavelength. Backscatter signals 106 and 108 are smooth continuous range-resolved backscatter signals indicative of uncollimated portions 44B and 46B divergently projected into the cloud atmosphere.

In FIG. 9B, graphs 110 includes horizontal axis 112, vertical axis 114 and backscatter signals 116 and 118. Horizontal axis 102 represents time and/or range within a cloud atmosphere. Vertical axis 104 represents signal strength of backscatter signals 116 and 118 backscattered by the cloud atmosphere and detected by an optical detector. Backscatter signals 116 and 118 correspond to third and fourth pulses of optical energy 44 and 46, respectively. Third pulse 44 of optical energy was generated by the first optical emitter having the first wavelength, and fourth pulse of optical energy was generated by the second optical emitter having the second wavelength. Backscatter signals 116 and 118 are range-resolved backscatter signals having scintillation spikes indicative of collimated portions (such as those depicted in FIG. 6A as 44A and 46A) projected into the cloud atmosphere.

By comparing backscatter signals 116 and 118 with backscatter signals 106 and 108, various metrics of SLDs within the cloud atmosphere can be calculated. For example, the size (e.g., diameter, volume, etc.) of SLDs, and/or the density of SLDs can be determined, based on various measures of the scintillation spikes. Also, various metrics of the small water droplets can be calculated based on the backscatter signals 106, 108, 116 and 118. For example, first and second modes of water droplets can be determined, based on comparisons between backscatter signals 108 and 108 with backscatter signals 116 and 118, respectively.

The following are non-exclusive descriptions of possible embodiments of the present invention.

Apparatus and associated methods relate to a system for calculating a metric of Super-cooled Large Droplets (SLDs) in a cloud atmosphere. The system includes an optical source configured to divergently project first and second pulses of optical energy about an optical axis. The system includes an optical control module configured to receive at least a portion of each of the first and second divergently projected pulses of optical energy and to direct the received portion of each of the first and second divergently projected pulses within a projection range. The system includes a collimator lens located within the projection range of the optical control module and configured to collimate a portion of each of the first and second pulses of optical energy directed by the optical control module therethrough into a cloud atmosphere. The system includes an optical window located within the projection range of the optical control module and configured to transmit an uncollimated portion of each of the first and second pulses of optical energy directed by the optical control module therethrough into a cloud atmosphere. The system includes an optical detector configured to detect and to generate first and second signals indicative of each of the first and second pulses of optical energy, respectively, backscattered by the cloud atmosphere. A difference between a first ratio and a second ratio of the collimated to the uncollimated portions corresponding to each of the first and second pulses of optical energy is greater than 0.10. The system also includes a processor configured to calculate, based on the generated first and second signals, a metric of SLDs in the cloud atmosphere.

The system of the preceding paragraph can optionally include, additionally and/or alternatively, any one or more of the following features, configurations and/or additional components:

A further embodiment of the foregoing system, wherein the optical control module can include a movable shutter configured to selectively obscure, when moved to an obscuring position, a portion of the divergently projected first and/or second pulse of optical energy.

A further embodiment of any of the foregoing systems, wherein the optical control module can include a Digital Micro-mirror Device (DMD). The control module can be configured to operate the DMD in a first mode for the first pulse of optical energy and in a second mode for the second pulse of optical energy.

A further embodiment of any of the foregoing systems, wherein a the DMD comprises a two-dimensional array of mirrors which are pivotable from nominal positions. The two-dimensional array can include a first region of pivotable mirrors and a second region of pivotable mirrors. The first region of pivotable mirrors can correspond to locations that, when in nominal positions, direct the first and/or second pulses of optical energy through the collimated lens. The second region of pivotable mirrors can correspond to locations that, when in nominal positions, direct the first and/or second pulses of optical energy through the optical window.

A further embodiment of any of the foregoing systems, wherein the first mode can include pivoting the pivotable mirrors located in the first region so as to direct the first and/or second pulses of optical energy away from the collimator lens. The second mode can include pivoting the pivotable mirrors located in the first region so as to direct the first and/or second pulses of optical energy through the collimator lens.

A further embodiment of any of the foregoing systems, wherein a difference between a first ratio and a second ratio of the collimated to the uncollimated portions corresponding to the first and second pulses of optical energy, respectively, can be greater than 0.50.

Any of the foregoing systems can include an optical absorption member located within the projection range of the optical control module and configured to absorb an absorbed portion of each of the first and second pulses of optical energy directed by the optical control module thereupon.

A further embodiment of any of the foregoing systems, wherein the collimator lens can be a cylindrical lens.

A further embodiment of any of the foregoing systems, wherein the optical control module can be further configured to control a rotational orientation of the cylindrical lens.

A further embodiment of any of the foregoing systems, wherein the optical source can include an optical fiber configured to transmit the generated pulses of optical energy and to divergently project, from a projection end, the transmitted pulses of optical energy over a field-of-view determined by a numerical aperture of the projection end.

A further embodiment of any of the foregoing systems, wherein the optical source can include first and second laser diodes. The first laser diode can be configured to generate pulses of optical energy having a first wavelength. The second laser diode can be configured to generate pulses of optical energy having a second wavelength.

A further embodiment of any of the foregoing systems, wherein the calculated metric of SLDs is average droplet size and/or density of SLDs.

Some embodiments relate to a method for calculating a metric of Super-cooled Large Droplets (SLDs) in a cloud atmosphere. The method includes generating first and second pulses of optical energy. The method includes divergently projecting the generated first and second pulses of optical energy over a solid angle greater than a predetermined threshold. The method includes redirecting at least a portion of each of the first and second divergently projected pulses of optical energy within a projection range. The method includes collimating a portion of the redirected first and/or second divergently projected pulses into a first projection volume of a cloud atmosphere. The method includes transmitting an uncollimated portion of the divergent first and/or second divergently projected pulses of optical energy into a second projection volume of the cloud atmosphere. The method includes detecting and generating first and second signals indicative of each of the first and second pulses of optical energy, respectively, backscattered by the cloud atmosphere. A difference between a first ratio and a second ratio of the collimated to the uncollimated portions corresponds to each of the first and second pulses of optical energy is greater than 0.10. The method also includes calculating, based on first and second generated signals, a metric of SLDs in the cloud atmosphere.

The method of the preceding paragraph can optionally include, additionally and/or alternatively, any one or more of the following features, configurations and/or additional components:

A further embodiment of the foregoing method, wherein redirecting at least the portion of each of the first and second divergently projected pulses of optical energy within the projection range can include moving a shutter configured to selectively obscure, when moved to an obscuring position, a portion of the divergently projected first and/or second pulses of optical energy.

A further embodiment of any of the foregoing methods, wherein redirecting at least a portion of each of the first and second divergently projected pulses of optical energy within the projection range can include pivoting each of a two-dimensional array of pivotable mirrors, the two-dimensional array of pivotable mirrors including a first region of pivotable mirrors corresponding to locations that when in nominal positions direct the first and/or second pulses of optical energy through a collimator lens, and a second region of pivotable mirrors corresponding to locations that when in nominal positions direct the first and/or second pulses of optical energy through an optical window.

A further embodiment of any of the foregoing methods, wherein a difference between a first ratio and a second ratio of the collimated to the uncollimated portions corresponding to the first and second pulses of optical energy, respectively, can be greater than 0.50.

Any of the foregoing methods can further include absorbing an absorption portion of each of the first and second pulses of optical energy;

Any of the foregoing methods can further include controlling a volume of the first projection volume of the cloud atmosphere.

A further embodiment of any of the foregoing methods, wherein divergently projecting the generated first and second pulses of optical energy over the solid angle greater than a predetermined threshold can include transmitting the generated first and second pulses of optical energy in an optical fiber. Divergently projecting the generated first and second pulses of optical energy over the solid angle greater than a predetermined threshold can also include projecting, from a projection end, the transmitted pulses of optical energy over a field-of-view determined by a numerical aperture of the projection end.

A further embodiment of any of the foregoing methods, wherein the calculated metric of SLDs can be average droplet size and/or density of SLDs.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A system for calculating a metric of Super-cooled Large Droplets (SLDs) in a cloud atmosphere, the system comprising:
    an optical source configured to divergently project first and second pulses of optical energy about an optical axis;
    an optical control module configured to receive at least a portion of each of the first and second divergently projected pulses of optical energy and to direct the received portion of each of the first and second divergently projected pulses within a projection range;
    a collimator lens located within the projection range of the optical control module and configured to collimate a portion of each of the first and second pulses of optical energy directed by the optical control module therethrough into a cloud atmosphere;
    an optical window located within the projection range of the optical control module and configured to transmit an uncollimated portion of each of the first and second pulses of optical energy directed by the optical control module therethrough into a cloud atmosphere;
    an optical detector configured to detect and to generate first and second signals indicative of each of the first and second pulses of optical energy, respectively, backscattered by the cloud atmosphere; and
    a processor configured to calculate, based on the generated first and second signals, a metric of SLDs in the cloud atmosphere.

2. The system of claim 1, wherein the optical control module comprises a movable shutter configured to selectively obscure, when moved to an obscuring position, a portion of the divergently projected first and/or second pulse of optical energy.

3. The system of claim 1, wherein the optical control module comprises a Digital Micro-mirror Device (DMD), the control module configured to operate the DMD in a first mode for the first pulse of optical energy and in a second mode for the second pulse of optical energy.

4. The system of claim 3, wherein a the DMD comprises a two-dimensional array of mirrors which are pivotable from nominal positions, the two-dimensional array including a first region of pivotable mirrors and a second region of pivotable mirrors, the first region of pivotable mirrors corresponding to locations that, when in nominal positions, direct the first and/or second pulses of optical energy through the collimated lens, the second region of pivotable mirrors corresponding to locations that, when in nominal positions, direct the first and/or second pulses of optical energy through the optical window.

5. The system of claim 4, wherein in the first mode, the pivotable mirrors located in the first region are pivoted so as to direct the first and/or second pulses of optical energy away from the collimator lens, wherein in the second mode, the pivotable mirrors located in the first region are pivoted so as to direct the first and/or second pulses of optical energy through the collimator lens.

6. The system of claim 1, wherein a difference between a first ratio and a second ratio of the collimated to the uncollimated portions corresponding to the first and second pulses of optical energy, respectively, is greater than 0.50.

7. The system of claim 1, further comprising:
    an optical absorption member located within the projection range of the optical control module and configured to absorb an absorbed portion of each of the first and second pulses of optical energy directed by the optical control module thereupon.

8. The system of claim 1, wherein the collimator lens is a cylindrical lens.

9. The system of claim 8, wherein the optical control module is further configured to control a rotational orientation of the cylindrical lens.

10. The system of claim 1, wherein the optical source comprises:
    an optical fiber configured to transmit the generated pulses of optical energy and to divergently project, from a projection end, the transmitted pulses of optical energy over a field-of-view determined by a numerical aperture of the projection end.

11. The system of claim 1, wherein the optical source comprises:
    first and second laser diodes, wherein the first laser diode is configured to generate pulses of optical energy having a first wavelength, and the second laser diode is configured to generate pulses of optical energy having a second wavelength.

12. The system of claim 1, wherein the calculated metric of SLDs is average droplet size or density of SLDs.

13. A method for calculating a metric of Super-cooled Large Droplets (SLDs) in a cloud atmosphere, the method comprising:
    generating first and second pulses of optical energy;
    divergently projecting the generated first and second pulses of optical energy over a solid angle greater than a predetermined threshold;
    redirecting at least a portion of each of the first and second divergently projected pulses of optical energy within a projection range;
    collimating a portion of the redirected first and/or second divergently projected pulses into a first projection volume of a cloud atmosphere;
    transmitting an uncollimated portion of the divergent first and/or second divergently projected pulses of optical energy into a second projection volume of the cloud atmosphere;
    detecting and generating first and second signals indicative of each of the first and second pulses of optical energy, respectively, backscattered by the cloud atmosphere; and
    calculating, based on first and second generated signals, a metric of SLDs in the cloud atmosphere.

14. The method of claim 13, wherein redirecting at least the portion of each of the first and second divergently projected pulses of optical energy within the projection range comprises:
    moving a shutter configured to selectively obscure, when moved to an obscuring position, a portion of the divergently projected first and/or second pulses of optical energy.

15. The method of claim 13, wherein redirecting at least a portion of each of the first and second divergently projected pulses of optical energy within the projection range comprises:

pivoting each of a two-dimensional array of pivotable mirrors, the two-dimensional array of pivotable mirrors including a first region of pivotable mirrors corresponding to locations that when in nominal positions direct the first and/or second pulses of optical energy through a collimator lens, and a second region of pivotable mirrors corresponding to locations that when in nominal positions direct the first and/or second pulses of optical energy through an optical window.

16. The method of claim 13, wherein a difference between a first ratio and a second ratio of the collimated to the uncollimated portions corresponding to the first and second pulses of optical energy, respectively, is greater than 0.50.

17. The method of claim 13, further comprising:
absorbing an absorption portion of each of the first and second pulses of optical energy.

18. The method of claim 13, further comprising:
controlling a volume of the first projection volume of the cloud atmosphere.

19. The method of claim 13, wherein divergently projecting the generated first and second pulses of optical energy over the solid angle greater than a predetermined threshold comprises:

transmitting the generated first and second pulses of optical energy in an optical fiber; and projecting, from a projection end, the transmitted pulses of optical energy over a field-of-view determined by a numerical aperture of the projection end.

20. The method of claim 13, wherein the calculated metric of SLDs is average droplet size and/or density of SLDs.

* * * * *